(12) United States Patent
Hoang

(10) Patent No.: US 10,583,179 B2
(45) Date of Patent: Mar. 10, 2020

(54) METHOD OF MANUFACTURING AND PURIFYING PROTHROMBIN COMPLEX CONCENTRATE FROM FRACTION III FOR INTRAVENOUS INJECTION AND A METHOD OF CURING AND PREVENTING HEMOPHILIA A WITH INHIBITORS OR HEMOPHILIA B IN PATIENTS INFECTED WITH HIV-1 AND HIV-2

(71) Applicant: Kieu Hoang, Agoura Hills, CA (US)

(72) Inventor: Kieu Hoang, Agoura Hills, CA (US)

( * ) Notice: Subject to any disclaimer, the term of this patent is extended or adjusted under 35 U.S.C. 154(b) by 117 days.

(21) Appl. No.: 15/090,033

(22) Filed: Apr. 4, 2016

(65) Prior Publication Data

US 2016/0287681 A1 Oct. 6, 2016

Related U.S. Application Data

(60) Provisional application No. 62/142,226, filed on Apr. 2, 2015.

(51) Int. Cl.
| | | |
|---|---|---|
| *A61K 9/19* | (2006.01) | |
| *A61K 38/48* | (2006.01) | |
| *A61K 9/00* | (2006.01) | |
| *A61K 9/16* | (2006.01) | |

(52) U.S. Cl.
CPC ........ *A61K 38/4833* (2013.01); *A61K 9/0019* (2013.01); *A61K 9/1688* (2013.01); *A61K 9/19* (2013.01); *A61K 38/4846* (2013.01); *C12Y 304/21005* (2013.01); *C12Y 304/21006* (2013.01); *C12Y 304/21021* (2013.01); *C12Y 304/21022* (2013.01)

(58) Field of Classification Search
None
See application file for complete search history.

(56) References Cited

U.S. PATENT DOCUMENTS

| | | | | |
|---|---|---|---|---|
| 6,124,273 A | * | 9/2000 | Drohan | A61K 9/0014 514/13.6 |
| 2013/0101579 A1 | * | 4/2013 | Bruckschwaiger | A61K 9/0019 424/130.1 |

FOREIGN PATENT DOCUMENTS

WO    WO 2013/116482    *    8/2013

OTHER PUBLICATIONS

Burnouf et al. (Haemophilia (2003), 9, 24-37) (Year: 2003).*

* cited by examiner

*Primary Examiner* — Sergio Coffa
(74) *Attorney, Agent, or Firm* — Merek, Blackmon & Voorhees, LLC

(57) ABSTRACT

The present subject matter is directed to a method of manufacturing and purifying an intraveneous injection of prothrombin complex concentration (PCC) from plasma Fraction III, comprising reconstituting a Fraction III paste in a buffer to create a Fraction III suspension; adjusting pH and temperature of the Fraction III suspension; performing PEG precipitation; centrifuging the Fraction III suspension and collecting a supernatant; filtering the supernatant; performing solvent detergent virus inactivation of the supernatant; undergoing weak anion exchange chromatography of the supernatant; twice washing and eluting two to three times; ultra-filtering the supernatant; adjusting pH of the supernatant; adjusting activity of a human factor IX of the supernatant; performing aseptic filtration and nano filtration for virus removal; and filling and lyophilizing to obtain the intraveneous injection of PCC.

10 Claims, 3 Drawing Sheets

METHOD OF MANUFACTURING AND PURIFYING PROTHROMBIN COMPLEX CONCENTRATE FROM FRACTION III FOR INTRAVENOUS INJECTION AND A METHOD OF CURING AND PREVENTING HEMOPHILIA A WITH INHIBITORS OR HEMOPHILIA B IN PATIENTS INFECTED WITH HIV-1 AND HIV-2

RELATED APPLICATIONS

The present patent application claims priority to provisional U.S. Patent Application No. 62/142,226 filed Apr. 2, 2015, which was filed by the inventor hereof and are incorporated by reference herein in its entirety.

TECHNICAL FIELD

The present subject matter relates to an intravenous injection of Prothrombin Complex Concentrate (PCC) manufactured from plasma Fraction III for Hemophilia B or Hemophilia A patients. In particular, the present subject matter is associated with methods of using an intravenous injection of the manufactured PCC for curing and preventing Hemophilia A with inhibitors and Hemophilia B patients infected with viruses HIV-1 and HIV-2.

BACKGROUND

Prothrombin complex concentrate (PCC) is a combination of human coagulation factors II, VII, IX, and X, usually prepared from human blood plasma. In clinical practice, PCC is administered to reach quick homeostasis, such as for bleeding episodes or Hemophilia A patients with factor VIII inhibitors. PCC may be used to reverse the effect of warfarin and other anti-coagulants and may be used when such a patient must undergo an emergency operation treatment.

Hemophilia A is known as classic hemophilia or factor VIII deficiency and is a genetic disorder. Hemophilia A occurs when factor VIII, a clotting protein, is missing or defective. Hemophilia B is a genetic disorder where the clotting protein factor IX is missing or defective and is less common than Hemophilia A.

SUMMARY

There are 19 existing and unknown new found proteins in this PCC formulation, among which eight are newly-found proteins KH 11, KH 12, KH 13, KH 14, KH 15, KH 16, KH 17, and KH 18.

According to the present subject matter, PCC may now be produced from plasma Fraction III paste, which includes eight newly-found proteins for intravenous injection to cure and to prevent HIV-1 and HIV-2.

An embodiment of the present subject matter is directed to the 19 existing and newly-found proteins present in the PCC extracted from Fraction III of human plasma. Of those, eight are newly-found proteins (KH 11, KH 12, KH 13, KH 14, KH 15, KH 16, KH 17, and KH 18) and 11 are existing proteins, which are processed and purified to make a product of PCC. With the addition of newly-found proteins, the intravenous solution of PCC not only stops replication of HIV-1 and HIV-2, but also prevents HIV-1 and HIV-2 virus infections.

An embodiment of the present subject matter is directed to a method of manufacturing and purifying an intraveneous injection of PCC from plasma Fraction III comprising the steps:

a) reconstituting a Fraction III paste in a buffer to create a Fraction III suspension;
b) adjusting pH and temperature of the Fraction III suspension;
c) performing PEG precipitation of the Fraction III suspension;
d) centrifuging the Fraction III suspension and collecting a supernatant;
e) filtering the supernatant with a 10CP+90SP filter;
f) performing solvent detergent virus inactivation of the supernatant;
g) undergoing weak anion exchange chromatography of the supernatant;
h) twice washing the supernatant and eluting two to three times;
i) ultra-filtering the supernatant with a 10 K membrane;
j) adjusting pH of the supernatant;
k) adjusting activity of a human factor IX of the supernatant;
l) performing aseptic filtration and nano filtration of the supernatant for virus removal; and
m) filling and lyophilizing the supernatant to obtain the intraveneous injection of PCC.

An embodiment of the present subject matter is directed to an intravenous injection of PCC produced according to the method of manufacturing and purifying an intraveneous injection of PCC from Fraction III.

An embodiment of the present subject matter is directed to a method of treatment for a patient comprising administering the intraveneous injection of PCC obtained from the method of manufacturing and purifying an intraveneous injection of PCC from Fraction III to a patient in need thereof, wherein the intravenous injection of PCC transforms or repairs damaged and sick cells to become healthy cells, wherein the intravenous injection of PCC protects cellular alterations, and wherein the intravenous injection of PCC sends signals to the patient's body to produce new cells that are healthy, thereby preventing the new cells from being affected by intracellular and extracellular damaging signals.

An embodiment of the present subject matter is directed to a method of stopping replication of HIV-1 and HIV-2 in a patient comprising administering the intravenous injection of PCC obtained from the method of manufacturing and purifying an intraveneous injection of PCC from Fraction III to a patient in need thereof.

An embodiment of the present subject matter is directed to a method of killing HIV-1 and HIV-2 in a patient comprising administering the intravenous injection of PCC obtained from the method of manufacturing and purifying an intraveneous injection of PCC from Fraction III to a patient in need thereof.

An embodiment of the present subject matter is directed to a method of preventing infection of HIV-1 and HIV-2 in a patient comprising administering the intravenous injection of PCC obtained from the method of manufacturing and purifying an intraveneous injection of PCC from Fraction III to a patient in need thereof.

An embodiment of the present subject matter is directed to a method of curing and preventing Hemophilia A with inhibitors in a patient comprising administering the intraveneous injection of PCC obtained from the method of manufacturing and purifying an intraveneous injection of PCC from Fraction III to a patient in need thereof.

DETAILED DESCRIPTION

Figure 1:
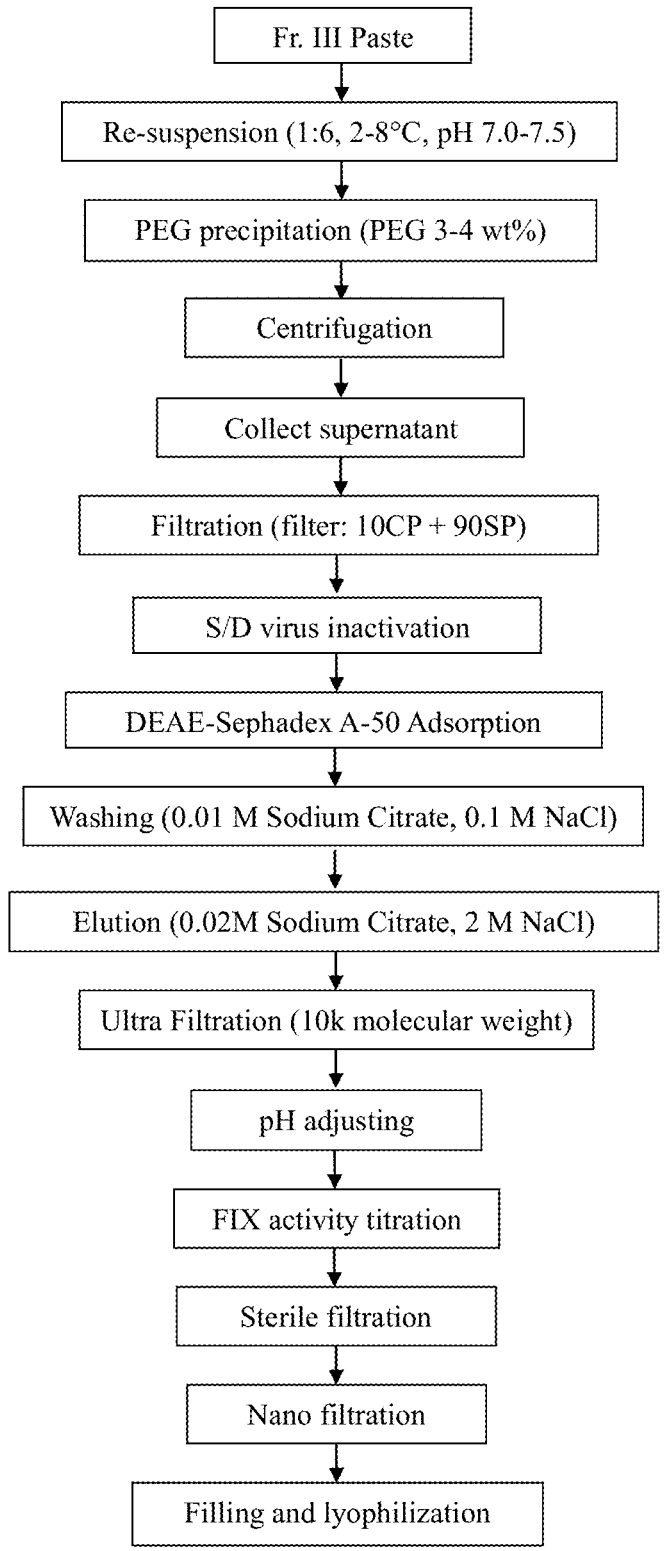
FIG. 1 is a flow chart depicting the production of PCC from Fraction III.
Figure 2:
FIG. 2 shows 2D electropherosis of PCC from Fraction III, which shows newly-found proteins KH 11, KH 12, KH 13, KH 14, KH 15, KH 16, KH 17, and KH 18.
Figure 3:
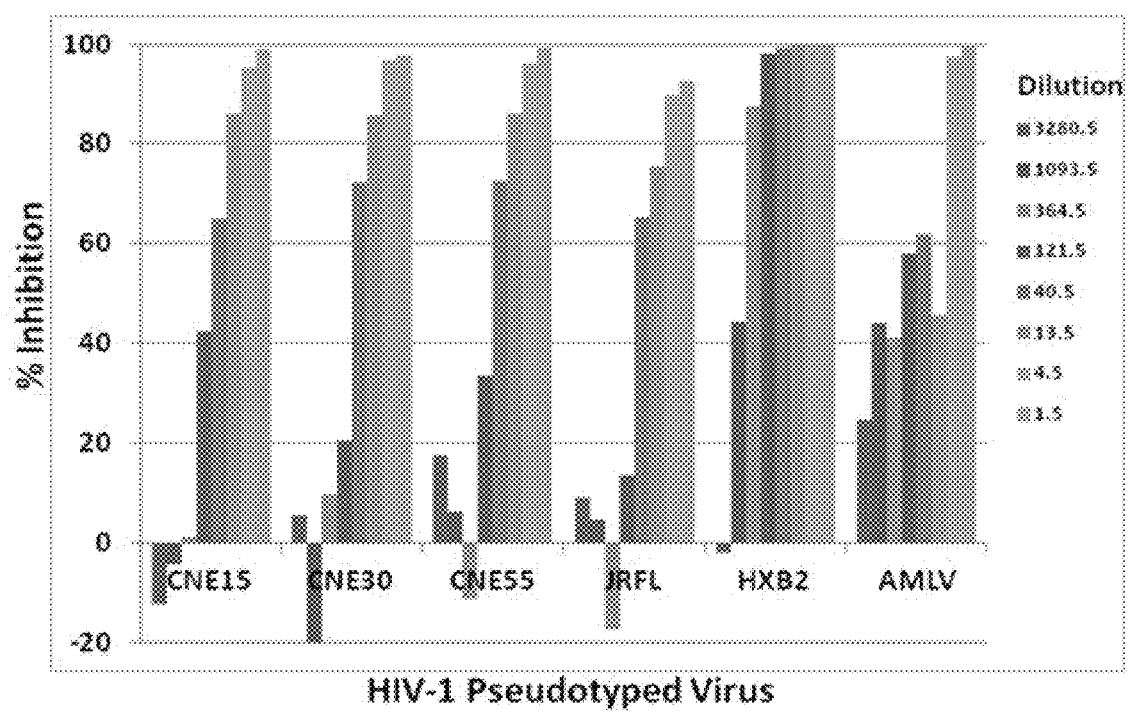
FIG. 3 shows the inhibition rate of AFCC RAAS in 5 HIV-1 strains and the control virus AMLV. Results show the inhibition rate is about 60% when the dilution is less than 1:40. Inhibition is also observed in the control virus AMLV. Cell toxicity is found in high concentrations via observation of cell morphology 48 hours after treatment.
Figure 4:
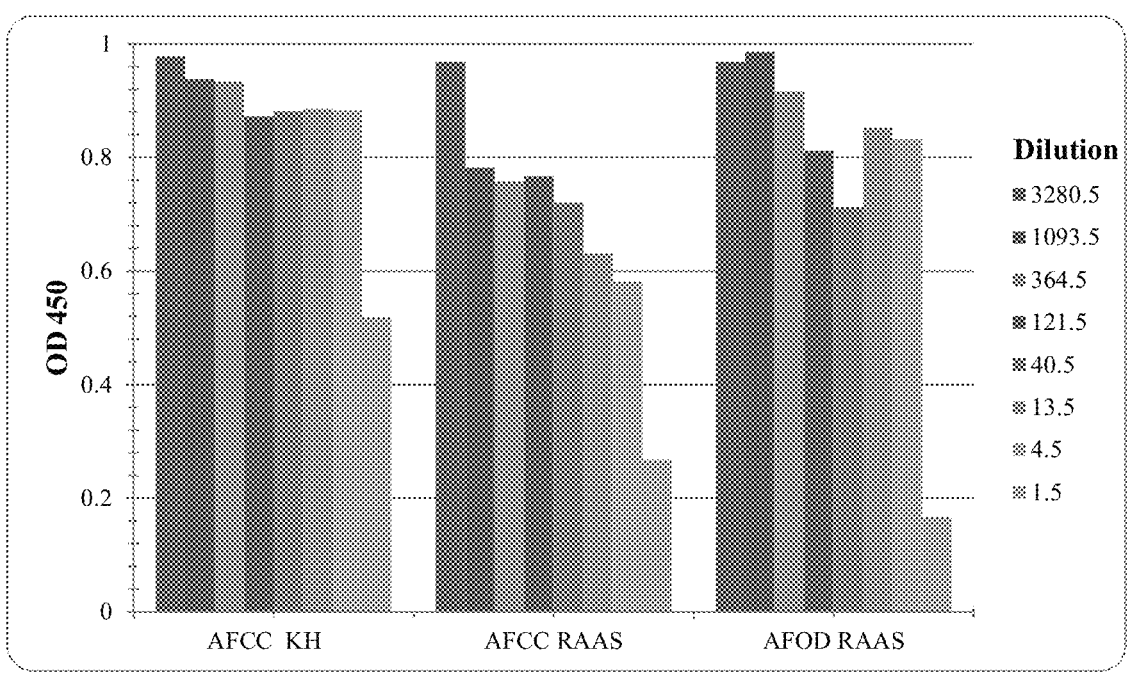
FIG. 4 shows the results of a cell toxicity test of AFCC RAAS. Test samples were diluted at 1:1.5 to start and then 1:4.5, 1:13.5, 1:40.5, 1:121.5, 1:364.5, 1:1093.5, and 1:3280.5, where the dilution was a three-fold dilution with eight dilutions in total. The test kit used was cell counting kit 8 (CCK-8), where the procedure was performed according to the manufacturer's manual. Results show some cell toxicity of RAAS, which likely causes the inhibition of HIV.

Unless defined otherwise all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language; however, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

An embodiment of the present subject matter is directed to a method of manufacturing and purifying an intraveneous injection of PCC from plasma Fraction III comprising the steps:
a) reconstituting a Fraction III paste in a buffer to create a Fraction III suspension;
b) adjusting pH and temperature of the Fraction III suspension;
c) performing PEG precipitation of the Fraction III suspension;
d) centrifuging the Fraction III suspension and collecting a supernatant;
e) filtering the supernatant with a 10CP+90SP filter;
f) performing solvent detergent virus inactivation of the supernatant;
g) undergoing weak anion exchange chromatography of the supernatant;
h) twice washing the supernatant and eluting two to three times;
i) ultra-filtering the supernatant with a 10 K membrane;
j) adjusting pH of the supernatant;
k) adjusting activity of a human factor IX of the supernatant;
l) performing aseptic filtration and nano filtration of the supernatant for virus removal; and
m) filling and lyophilizing the supernatant to obtain the intraveneous injection of PCC.

An embodiment of the present subject matter is directed to an intraveneous injection of PCC produced according to the method of manufacturing and purifying an intraveneous injection of PCC from Fraction III. An embodiment of the present subject matter is directed to purified PCC containing eight newly-found proteins, namely KH 11, KH 12, KH 13, KH 14, KH 15, KH 16, KH 17, and KH 18. In an embodiment, Fraction III is obtained by Cohn ethanol fractionation of plasma and comprises newly-found proteins KH 11, KH 12, KH 13, KH 14, KH 15, KH 16, KH 17, and KH 18.

In an embodiment of the present subject matter, the Fraction III suspension is resuspended in a buffer containing up to 10% heparin and up to 80 mM sodium citrate and pH and temperature are adjusted. In an embodiment of the present subject matter, the Fraction III suspension is precipitated with PEG at a final concentration of 4.0-10.0 wt %. In an embodiment of the present subject matter, the solvent detergent virus inactivation comprises adding TNBP to a final concentration of 0.3% and Tween-80 to a final concentration of 1.0% at 25° C. for 6 hours. In an embodiment of the present subject matter, the weak anion exchange chromatography is DEAE A-50 at a final concentration of 4-10 wt %.

In an embodiment of the present subject matter, washing the supernatant comprises using a washing buffer comprising up to 1.0 M sodium citrate and up to 2.0 M NaCl for two times. In an embodiment of the present subject matter, washing the supernatant comprises using a washing buffer comprising up to 2.0 M sodium citrate and up to 2.0 M NaCl for two to three times. In an embodiment of the present subject matter, the aseptic filtration is at 0.22 In an embodiment of the present subject matter, the nano filtration is at 20 nm.

An embodiment of the present subject matter is directed to a method of treatment for a patient comprising administering the intraveneous injection of PCC obtained from the method of manufacturing and purifying an intraveneous injection of PCC from Fraction III to a patient in need thereof, wherein the intraveneous injection of PCC transforms or repairs damaged and sick cells to become healthy cells, wherein the intraveneous injection of PCC protects cellular alterations, and wherein the intraveneous injection of PCC sends signals to the patient's body to produce new cells that are healthy, thereby preventing the new cells from being affected by intracellular and extracellular damaging signals.

An embodiment of the present subject matter is directed to a method of stopping replication of HIV-1 and HIV-2 in a patient comprising administering the intraveneous injection of PCC obtained from the method of manufacturing and purifying an intraveneous injection of PCC from Fraction III to a patient in need thereof. In an embodiment, the patient is a Hemophilia B patient.

An embodiment of the present subject matter is directed to a method of killing HIV-1 and HIV-2 in a patient comprising administering the intravenous injection of PCC obtained from the method of manufacturing and purifying an intraveneous injection of PCC from Fraction III to a patient in need thereof. In an embodiment, the patient is a Hemophilia B patient.

An embodiment of the present subject matter is directed to a method of preventing infection of HIV-1 and HIV-2 in a patient comprising administering the intravenous injection of PCC obtained from the method of manufacturing and purifying an intraveneous injection of PCC from Fraction III to a patient in need thereof. In an embodiment, the patient is a Hemophilia B patient.

An embodiment of the present subject matter is directed to a method of curing and preventing Hemophilia A with inhibitors in a patient comprising administering the intraveneous injection of PCC obtained from the method of manufacturing and purifying an intraveneous injection of PCC from Fraction III to a patient in need thereof.

In an embodiment, any of these or any combination of the eight newly-found proteins has the ability to stop replication of HIV-1 and HIV-2. In an embodiment, any of these or any combination of the eight newly-found proteins has the ability to kill HIV-1 and HIV-2. In an embodiment, any of these or any combination of the eight newly-found proteins has the ability to prevent infection of HIV-1 and HIV-2. In an embodiment, any of these or any combination of the newly-found proteins has the following abilities: 1) transform/repair DAMAGED and SICK cells to become KH GOOD healthy cells, 2) protect cellular alterations, and 3) signal the body to produce new, healthy cells immunized from intracellular and extracellular damaging signals. In an embodiment, any of these or any combination of the 19 proteins in PCC from Fraction III (Fr. III) has the ability to stop replication of HIV-1 and HIV-2, kill HIV-1 and HIV-2, and prevent infection of HIV-1 and HIV-2.

EXAMPLES

In Vitro Testing

The intraveneous injection of PCC with the eight newly-found proteins was tested by the Comprehensive National AIDS Research Center, Tsinghua University in China, which concluded that PCC having the code name AFCC RAAS has the ability to stop replication of and kill the HIV virus. The supplementary results of the neutralization of HIV-1 Env-pseudotyped virus follow.

Samples and Control

The test sample used was AFCC RAAS.

Five strains of the virus were tested. In particular, the strains tested include BC recombinant subtype viruses CNE15 and CNE30, CRFO1_AE recombinant subtype virus CNE55, and standard HIV-1 virus strains HXB2 and JRFL. All of the HIV-1 virus strains have CCR5 receptor affinity, with the exception of HXB2, which has CXCR4 receptor affinity.

The control virus used was AMLV.

Test Method

The test samples were diluted at 1:1.5 to start and then at 1:4.5, 1:13.5, 1:40.5, 1:121.5, 1:364.5, 1:1093.5, and 1:3280.5. The dilution was a three-fold dilution with eight dilutions in total.

Results

FIG. 3 shows the inhibition rate of AFCC RAAS in the five HIV-1 strains and the control virus AMLV. Results indicate the inhibition rate is about 60% when the dilution was less than 1:40 and inhibition also was observed in the control virus AMLV. Cell toxicity was found in high concentrations via observing cell morphology 48 hours after treatment. The cell toxicity test was then conducted.

FIG. 4 shows the results of the cell toxicity test. In particular, the toxicity of AFCCKH, AFOD RAAS 101, and AFCC RAAS were tested. Test samples were diluted at 1:1.5 to start and then at 1:4.5, 1:13.5, 1:40.5, 1:121.5, 1:364.5, 1:1093.5, and 1:3280.5. The dilution was a three-fold dilution with eight dilutions in total. The test kit was cell counting kit 8 (CCK-8), and the procedure was carried out according to manufacturer's manual. Results indicate there is some cell toxicity of RAAS. Thus, inhibition of HIV virus is likely caused by cell toxicity.

To decrease the toxicyte to cell, and ensure the high inhibition of virus at high protein concentration, the protein concentration may be further increased. Furthermore, the cell culture medium, DMEM+10% FBS, may be used as the diluent of products when preparing the samples.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

I claim:

1. A method of manufacturing and purifying an intravenous injection of prothrombin complex concentration (PCC) from plasma Fraction III, comprising the steps:

a) reconstituting a Fraction III paste in a buffer to create a Fraction III suspension;

b) adjusting pH and temperature of the Fraction III suspension;

c) performing polyethylene glycol (PEG) precipitation of the Fraction III suspension;

d) centrifuging the precipitated Fraction III suspension and collecting a supernatant resulting from said centrifugation;

e) filtering the supernatant with a 10CP+90SP filter to produce a filtered supernatant;

f) performing solvent detergent virus inactivation of the filtered supernatant;

g) undergoing weak anion exchange chromatography of the filtered supernatant;

h) twice washing the filtered supernatant with a washing buffer comprising Na citrate and NaCl and additionally eluting two to three times with an eluting buffer, wherein the washing buffer comprises up to 2.0 M sodium citrate and up to 2.0 M NaCl and the eluting buffer comprises up to 1.0 M sodium citrate and up to 2.0 M NaCl, to produce an elution;
i) ultra-filtering the elution with a 10K membrane;
j) adjusting pH of the elution;
k) adjusting activity of a human factor IX of the elution;
l) performing aseptic filtration and nano filtration of the elution for virus removal to produce a filtered elution; and
m) filling and lyophilizing the filtered elution to obtain the intravenous injection of PCC.

2. The method of claim 1, wherein the plasma Fraction III is obtained by Cohn ethanol fractionation of plasma comprising newly-found proteins KH 11, KH 12, KH 13, KH 14, KH 15, KH 16, KH 17 and KH 18.

3. The method of claim 1, wherein the Fraction III suspension is resuspended in a buffer containing up to 10% heparin and up to 80 mM sodium citrate and pH and temperature are adjusted.

4. The method of claim 1, wherein the Fraction III suspension is precipitated with PEG at a final concentration of 4.0-10.0 wt %.

5. The method of claim 1, wherein the solvent detergent virus inactivation comprises adding TNBP to a final concentration of 0.3% and Tween-80 to a final concentration of 1.0% at 25° C. for 6 hours.

6. The method of claim 1, wherein the weak anion exchange chromatography is DEAE A-50 at a final concentration of 4-10 wt %.

7. The method of claim 1, wherein the washing the filtered supernatant in step h comprises washing with the washing buffer having around 0.01 M sodium citrate and around 0.1 M NaCl for two times.

8. The method of claim 7, wherein the washing the filtered supernatant in step h comprises washing with the non-alcoholic washing buffer having around 0.02 M sodium citrate and 2.0 M NaCl for two to three times.

9. The method of claim 1, wherein the aseptic filtration is at 0.22 µm.

10. The method of claim 1, wherein the nano filtration is at 20 nm.

* * * * *